(12) United States Patent
Lawandy

(10) Patent No.: US 6,633,370 B2
(45) Date of Patent: Oct. 14, 2003

(54) QUANTUM DOTS, SEMICONDUCTOR NANOCRYSTALS AND SEMICONDUCTOR PARTICLES USED AS FLUORESCENT CODING ELEMENTS

(75) Inventor: Nabil M. Lawandy, North Kingstown, RI (US)

(73) Assignee: Spectra Science Corporation, Providence, RI (US)

( * ) Notice: Subject to any disclaimer, the term of this patent is extended or adjusted under 35 U.S.C. 154(b) by 122 days.

(21) Appl. No.: 09/801,479

(22) Filed: Mar. 7, 2001

(65) Prior Publication Data
US 2001/0033371 A1 Oct. 25, 2001

Related U.S. Application Data
(60) Provisional application No. 60/187,607, filed on Mar. 7, 2000.

(51) Int. Cl.⁷ .............................................. G06K 9/74
(52) U.S. Cl. ............................................. 356/71; 235/454
(58) Field of Search ............................ 356/71; 235/454, 235/487, 494, 491

(56) References Cited

U.S. PATENT DOCUMENTS

| | | | | |
|---|---|---|---|---|
| 3,513,320 A | | 5/1970 | Weldon ..................... 250/219 |
| 5,046,841 A | * | 9/1991 | Juds et al. .................... 356/71 |
| 5,128,528 A | | 7/1992 | Heninger .................... 235/470 |
| 5,434,878 A | | 7/1995 | Lawandy ..................... 372/43 |
| 5,448,582 A | | 9/1995 | Lawandy ..................... 372/42 |
| 5,568,251 A | * | 10/1996 | Davies et al. ................. 356/71 |
| 5,682,103 A | * | 10/1997 | Burrell ....................... 250/556 |
| 5,881,886 A | | 3/1999 | Lawandy .................... 209/3.3 |
| 5,990,479 A | | 11/1999 | Weiss et al. ................. 250/307 |
| 6,057,561 A | | 5/2000 | Kawasaki et al. ............. 257/94 |
| 6,114,038 A | | 9/2000 | Castro et al. .......... 428/402.24 |
| 6,194,213 B1 | | 2/2001 | Barbera-Guillem ......... 435/968 |
| 6,207,229 B1 | | 3/2001 | Bawendi et al. ............ 427/215 |
| 6,207,392 B1 | | 3/2001 | Weiss et al. .................. 435/7.1 |
| 6,259,506 B1 | | 7/2001 | Lawandy .................... 349/193 |
| 6,296,189 B1 | | 10/2001 | Lawandy et al. ........... 235/491 |

FOREIGN PATENT DOCUMENTS

WO     WO-9614206     5/1996

OTHER PUBLICATIONS

*International Search Report* for PCT Patent Application No. PCT/US01/07328. Filed Mar. 7, 2001.

Chan et al. *"Quantum Dot Bioconjugates for Ultrasensitive Nonisotopic Detection."* http://www.sciencemag.org. Jun. 7, 1999.

Bruchez, Jr. et al. *"Semiconductor Nanocrystals as Fluorescent Biological Labels."* http://www.sciencemag.org. Jun. 3, 1999.

* cited by examiner

Primary Examiner—Karl D. Frech
Assistant Examiner—Jamara Franklin
(74) Attorney, Agent, or Firm—Harrington & Smith, LLP

(57) ABSTRACT

A method is disclosed for obtaining information about an object, as is a system operating in accordance with the method. The method includes steps of (a) placing a plurality of regions onto the object, each region being capable of emitting a predetermined wavelength of light; (b) detecting the light; and (c) decoding information from the detected light. At least one of the regions contains semiconductor particles having a radius larger than a quantum dot radius for a corresponding semiconductor material, and a chemical composition selected to provide the predetermined wavelength of light. The semiconductor material contains at least one of a Group II–IV alloy, or a Group III–V alloy, or a compound comprised of an indirect bandgap material, such as Si or Ge. The concentrations of the alloy or compound constituent elements are preselected to provide the predetermined emission wavelength. The semiconductor material may further include a selected dopant.

18 Claims, 3 Drawing Sheets

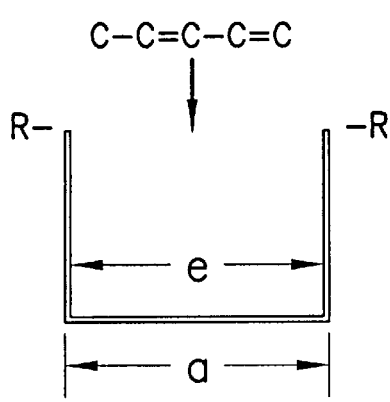
FIG. 1
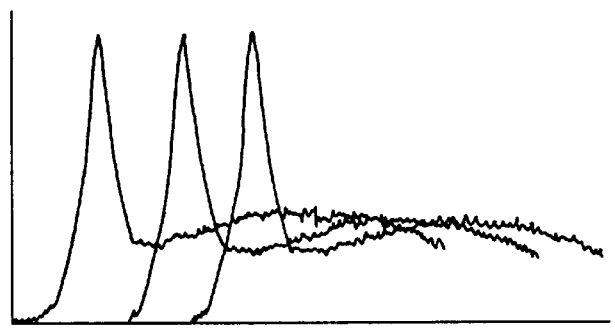
FIG. 4
$$E_p = \frac{h^2 n^2}{8ma^2}$$ EQUATION 1
$$\Delta E_{singlet}^{h \to n-1} = \frac{h^2(2n-1)}{8ma^2}$$ EQUATION 2
$$\Sigma = E_{gap} + \frac{h^2}{8ma^2}$$ EQUATION 3
$$\Delta \upsilon \sim V_F / \alpha$$ EQUATION 4
$$\frac{h}{8maV_F}$$ EQUATION 5
$$\alpha = \frac{h}{8mV_F} = 4nm$$ EQUATION 6
FIG. 2

$$\frac{N_s}{N_b} \sim \frac{3d}{R} \quad \text{EQUATION 7}$$

$$\text{FluorescentOutput} \approx I_o \times \sigma \times \frac{I_o}{2I_o + I_s} \times QE(\%) \quad \text{EQUATION 8}$$

$$I_s = \frac{h\nu}{\sigma T} \quad \text{EQUATION 9}$$

$$I_o \approx I_s \rightarrow \frac{h\nu \times QE(\%)}{3T} \quad \text{EQUATION 10}$$

$$\frac{Dye}{QD} \approx \frac{(QE)_{dye}}{(QE)_{QD}} \times \frac{T_{QD}}{T_{dye}} = \frac{75}{25} \times \frac{10^{-6}}{10^{-9}} \approx 3 \times 10^3 \quad \text{EQUATION 11}$$

FIG.5

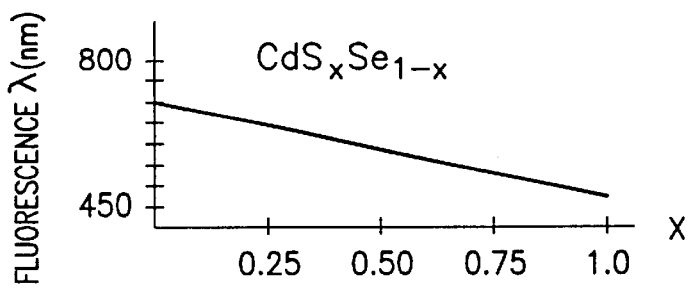

FIG.6

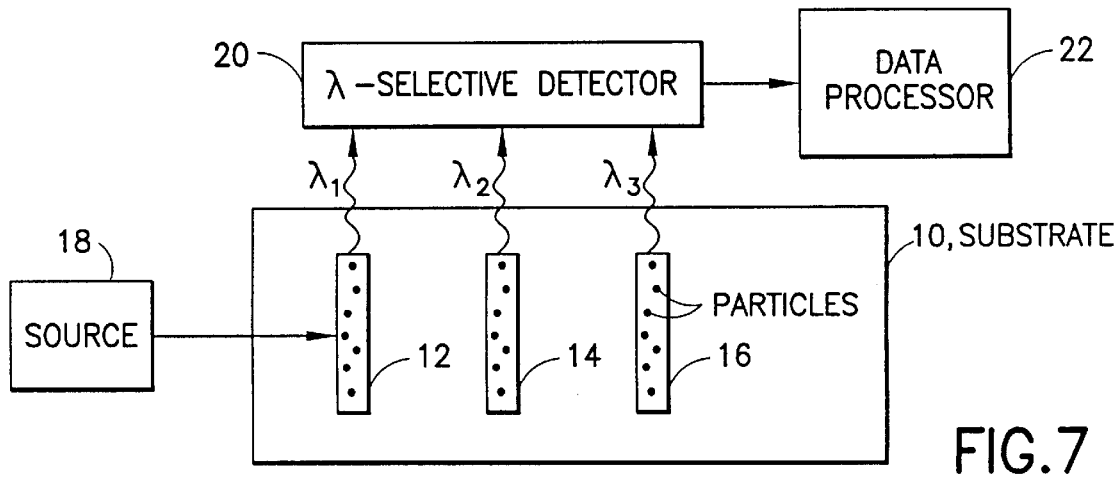

FIG.7

QUANTUM DOTS, SEMICONDUCTOR NANOCRYSTALS AND SEMICONDUCTOR PARTICLES USED AS FLUORESCENT CODING ELEMENTS

This application claims the benefit of Provisional Application No. 60/187,607, filed Mar. 7, 2000.

FIELD OF THE INVENTION

This invention relates generally to optical emitters and, in particular, to the use of semiconductor quantum dots, nanocrystals and particles as fluorescent coding elements.

BACKGROUND OF THE INVENTION

Semiconductor quantum dots are simple inorganic solids typically consisting of a hundred to a hundred thousand atoms. They emit spectrally resolvable energies, have a narrow symmetric emission spectrum, and are excitable at a single wavelength. Semiconductor quantum dots have higher electron affinities than organic polymers, such as those used as hole conductors in current display technology. They offer a distinct advantage over conventional dye molecules in that they are capable of emitting multiple colors of light. In addition, semiconductor quantum dots are size tunable, and when used as luminescent centers for electron hole recombination for electroluminescent illumination, their emission color is also size tunable. Another advantage is that the quantum dots are photochemically stable under UV excitation. Reference in this regard may be had to an article entitled: "Semiconductor Nanocrystals as Fluorescent Biological Labels" (M.Bruchez Jr. et al, Science (281), 1998).

Because semiconductor quantum dots emit a narrow linewidth, are efficient emitters, and are tunable by their quantum size effect, they are suitable for coding, labeling and authentication, applications. Another advantage associated with semiconductor quantum dots, also referred to as nanocrystals, is that they may be universally excited utilizing one UV source and therefore there is no need for multiple sources.

However, further investigation of the physical properties and interactions of quantum dots reveal some impediments to their use in practical applications.

One of the phenomena that quantum dots exhibit is chromophore tuning related to their quantum size, known as the "Quantum Size Effect". Dyes utilizing nanocrystals are exemplary systems for testing the "particle in 1-D box" model of quantum mechanics as shown in FIG. 1. This is because, among other things, they exhibit absorption and emission characteristics and may be optically directed with nonlinear optics (e.g. $X^{(3)}$).

Reference in this regard may be had to Kuhn, H.: *Progress in the Chemistry of Organic Natural Products*, ed. by D. L .Zechmeister, Vol. 16 (Springer, Wien 1959) p.17, and also to Försterling, H. D., H. Kuhn: *Physikalische Chemie in Experimenten. Ein Praktikum* (Verlag Chemie, Weinheim/ Bergstr.1971) p.373.

As an example, thiacyanine dyes (MW~600 a.m.u.) with a quantum dot size (a) of approximately 1.5 nm, and an emission wavelength ($\lambda$) of 500 nm, exhibit the characteristics shown in equations 1 and 2 of FIG. 2.

However, there are limits to the tunability that may be achieved by the quantum size effect. It is well known that the energy gap and excitation emission can be tuned by size according to equation 3 shown in FIG. 2. However, electrons and holes have "collisions" with the walls and broaden the excitation line ($\upsilon$) according to equation 4, where $V_F$ is a Fermi velocity ~$10^5$m/sec.

For example, using the quantum dot size of a=4 nm, the change in the excitation line ($\Delta\upsilon\nu$) would be $2.5\times10^{13}$ with a corresponding wavelength spread ($\Delta\lambda$) of 30 nm at 600 nm. A quantum dot size of 2 nm exhibits a wavelength spread ($\Delta\lambda$) of 60 nm at 600 nm.

In general, quantum dots smaller than 2 nm will have emission lines broader than dyes, as shown in FIG. 3.

As the quantum size shifts, the ratio of the shift in size and the resulting change in line width is shown in equation 5 of FIG. 2. When the shift to width ratio becomes unity, tuning is no longer effective for coding. The quantum size resulting in a shift to width ratio of 1 is 4 nm, as determined by equation 6 of FIG. 2. Thus, quantum dots larger than 4 nm will have shifts less then the emission linewidth.

In summary of the analysis of the characteristics of semiconductor quantum dots thus far, when coding and labeling with semiconductor nanocrystals or quantum dots, the following considerations should be taken into account:

1) The room temperature linewidth is approximately 30 nm ($2.5\times10^{13}$ sec$^{-1}$) as opposed to dyes which typically have 40–60 nm linewidths.
2) Separate peaks require $2\sigma$ separation of approximately 60 nm as opposed to dyes with 90 nm separation requirements.
3) A code density of $2^M-1$ may be achieved where M is the number of resolvable quantum dot emission peaks.

Combinatorial coding with quantum dots also presents complications related to trap states. Quantum dots have broad secondary peaks joining the excitonic emission as shown in FIG. 4. At 30% quantum efficiency, this broad peak has an amplitude half as high as the narrow 20 nm wide emission. As a result, the overlapping broad peaks restrict combinatorial coding with quantum dots even more than dyes.

Another factor to be considered when utilizing semiconductor quantum dots for coding and labeling applications is that the quantum efficiency of a quantum dot is affected by the interaction of carriers with the surfaces of the quantum dot. Surface atoms are not a bulk phase and are not generally amenable to lattice matched passivation (e.g., ZnS shell).

Reference in this regard may be had to "Quantum Dot Bioconjugates for Ultrasensitive Nonisotopic Detection", by Chan, W. C., Nie, S., Science, 281(5385):2016.

The ratio of surface atoms to bulk in a quantum dot is shown by equation 7 of FIG. 5, where d is a lattice constant. For a quantum size of 3 nm and a lattice constant of 0.3 nm, the ratio $N_s/N_b$ from equation 7 is approximately 30–40%, and therefore the quantum efficiency is approximately equal to R. Thus, the smaller the quantum dot, the lower the quantum efficiency, which further limits size tuning.

Semiconductor nanocrystals and quantum dots typically have quantum efficiencies of 5%–25% after some form of passivation. They are primarily comprised of surface or interface atoms which trap photo-carriers in picoseconds and relax with microsecond decays. This slow decay makes even their pulsed (flash lamp) excitation saturate at $I_s=10$ KW/cm$^2$. This is in contrast to dye chromophores which have 30%–95% quantum efficiencies, for example, $I_s$~MW/cm$^2$, and may in some instances produce amplification.

A comparison of the light output of quantum dots and dye chromophores may be made using the following relationships shown in FIG. 5. The fluorescent output is shown by equation 8, the saturation intensity ($I_s$) is shown by equation 9, and the maximum output ($I_o$~$I_s$) is derived from equation 10. The ratio of light output from a dye and quantum dots (Dye/QD) is approximately $3 \times 10^3$ as shown by equation 11.

It has been stated in prior art publications that the fluorescence intensity of a single quantum dot is equivalent to that of approximately 20 rhodamine molecules. However, when compared on an equivalent molecular weight basis, the results are quite different. For example, a comparison of a quantum dot structure with a CdSe core (excluding the ZnS shell) having a mass of approximately 100,000 a.m.u. with a Rhodamine6G (R6G) molecule having a mass of approximately 500 a.m.u., shows a relative intensity ratio ($I_{R6G}/I_{QD}$) of 10 when compared on an equivalent molecular weight basis.

While quantum dots are known to be photochemically stable under UV excitation, the utilization of UV sources involves some disadvantages including UV decomposition of synthesis products, singlet $O_2$ generation and reactions, and energetic recombination, trapping and photodegradation of the nanocrystals.

Another aspect of the photo-stability of semiconductor quantum dots to be considered is photo-darkening. Occurrences of photo-darkening are known in the applications utilizing semiconductor quantum dots, particularly with glass-based and polymer passivation. This is further complicated by the fact that the degree of passivation may not be universal or consistent and thus may vary with each semiconductor. This is disadvantageous when using semiconductor nanocrystals as optical or e-beam phosphors.

It has also been stated in the prior art that the quantum dot emission (time constant $t_{1/2}=960$ s) is nearly 100 times as stable as rhodamine 6G(R6G) ($t_{1/2}=10$ s) against photobleaching. However, on an equivalent mass basis, after approximately 1 minute of exposure, the intensity of R6G ($I_{R6G}$) is approximately the same as the intensity of the quantum dot structure ($I_{QD}$) In addition, dyes often recover from photobleaching while quantum dots typically do not.

It can be seen then that size tuning of quantum dots may yield less than optimum results, in particular when utilizing semiconductor quantum dots for fluorescence labeling and coding applications. As mentioned above, some disadvantages associated with practical applications include the fact that smaller dots ($\leq 2$ nm) create wider emissions and even lower quantum efficiencies, while sizes larger than 4 nm produce shifts smaller than a linewidth. In addition, quantum dots are difficult to passivate on a consistent basis and exhibit broad spectrum (<100 nm) trap emission and photobleaching. As was shown above, on a volume or mass basis, quantum dots are less optically efficient than dyes, and quantum dots offer significantly less coding capacity than dyes per unit wavelength.

SUMMARY OF THE INVENTION

The foregoing and other problems are overcome by methods and apparatus in accordance with embodiments of this invention.

A method is disclosed for obtaining information about an object, as is a system operating in accordance with the method. The method includes steps of (a) placing a plurality of regions onto the object, each region being capable of emitting a predetermined wavelength of light; (b) detecting the light; and (c) decoding information from the detected light. At least one of the regions contains semiconductor particles having a radius larger than a quantum dot radius for a corresponding semiconductor material, and a chemical composition selected to provide the predetermined wavelength of light. The semiconductor material contains at least one of a Group II–VI alloy, or a Group III–V alloy, or a compound comprised of an indirect bandgap material, such as Si or Ge. The concentrations of the alloy or compound constituent elements are preselected to provide the predetermined emission wavelength. The semiconductor material may further include a selected dopant.

In some embodiments (e.g., some Group II–VI and Group III–V embodiments) the semiconductor material alloy has the form $AB_xC_{1-x}$, where A, B and C are each a different element, and in this case in at least two of the plurality of regions the value of x can be made different.

BRIEF DESCRIPTION OF THE DRAWINGS

The above set forth and other features of the invention are made more apparent in the ensuing Detailed Description of the Invention when read in conjunction with the attached Drawings, wherein:

FIG. 1 depicts the "particle in a 1-D box" theory of quantum mechanics;

FIG. 2 depicts various equations related to the tunability of quantum dot particles;

FIG. 4 illustrates exemplary secondary peaks joining the secondary emission;

FIG. 5 depicts equations related to the ratio of surface atoms to bulk and to the light output of quantum dots;

FIG. 6 is a graph depicting emission wavelength versus concentration for a Group II–VI semiconductor material that is suitable for practicing this invention; and FIG. 7 shows the use of the improved fluorescent emission materials in an exemplary coding and identification application.

DETAILED DESCRIPTION OF THE INVENTION

Figure 3:
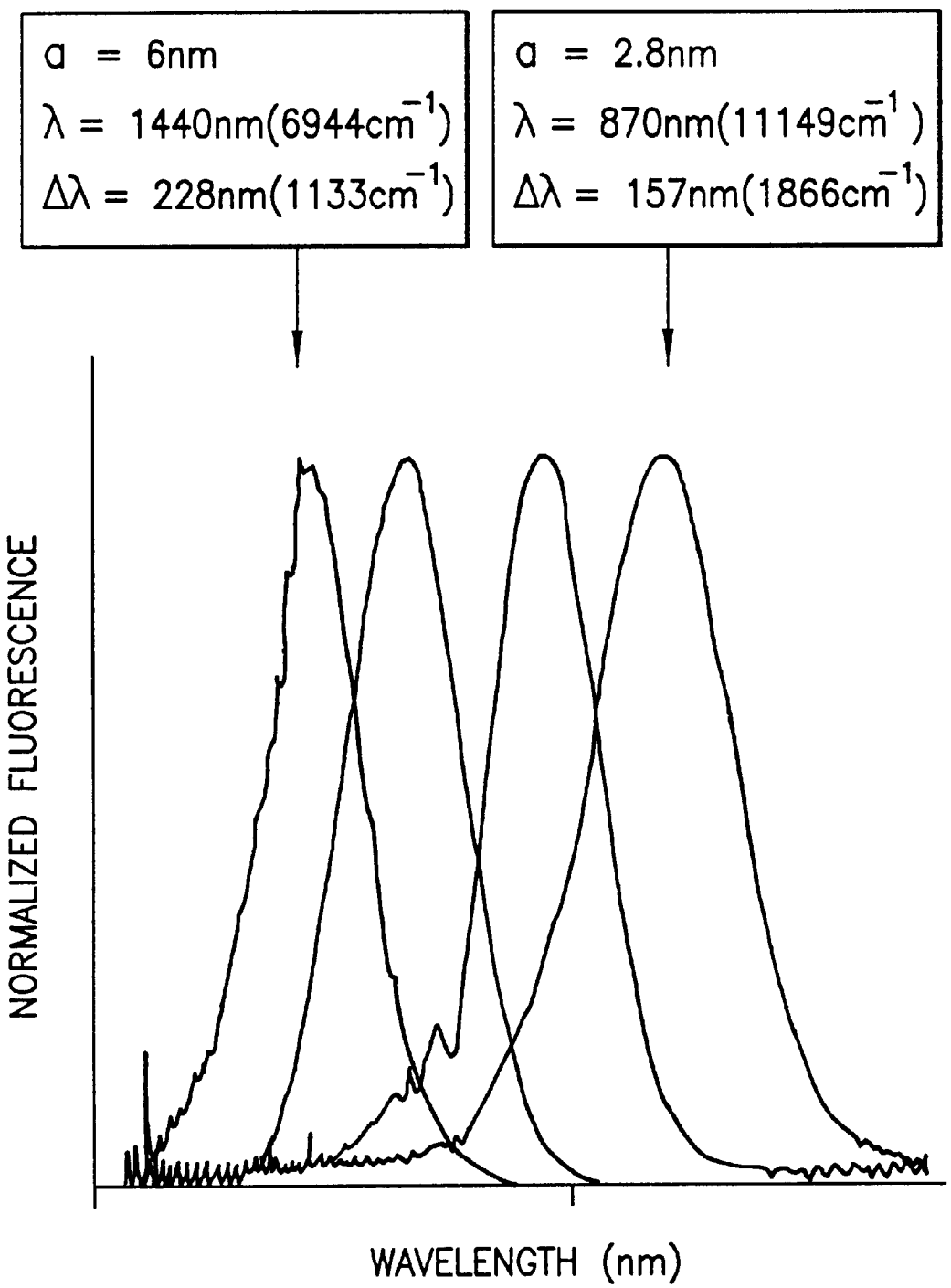
FIG. 3 shows typical emission lines for quantum dots smaller than 2 nm.

While the general trend is to utilize semiconductor quantum dots that are progressively smaller, the inventor has realized that utilization instead of larger semiconductor particles is advantageous for a number of reasons.

First, larger semiconductor particles have a much lower surface to volume atom ratio. For example, for a particle having a radius, R, of 25 nm, the surface to volume atom ratio is 4%. This contrasts to a quantum dot having a radius in the range of about 3 nm to 10 nm, where the surface to volume atom ratio may exceed 10%.

Second, larger particles have much higher quantum efficiencies (approaching 100%), as most of the recombination of electron-hole pairs takes place in the bulk.

Third, larger particles have insignificant trap state emission, thereby making sharper fluorescence lines.

In accordance with the invention, a further advantage of the use of larger semiconductor quantum dots is that the emission from larger semiconductor particles is adjusted or tuned by selective alloying of the semiconductor composition.

Example compositions include the Group II–VI tertiary materials $CdS_xS_{1-x}$, and $ZnS_xSe_{1-x}$, as well as tertiary and quaternary Group III–V materials, and material systems including indirect bandgap materials such as Si and Ge. Various dopants can also be employed, such as Mn and Cu. The alloying of the semiconductor can also be used to shift the dopant line, and can also affect the bandgap.

Thus, size tuning by alloying the semiconductor composition, using doped or undoped materials, allows for a wider range of emission frequencies than previously accomplished with smaller particles, such as quantum dots.

It is noted that a quantum dot may be defined to have a radius comparable to the radius of an exciton (electron-hole pair) in the semiconductor material. This is extended to semiconductor particles used for wavelength encoding applications, such as in authentication, validation and identification applications. These applications can be employed in, for example, genomics and combinatorial chemistry for uniquely encoding objects and structures with the particles and nanocrystals in accordance with these teachings.

FIG. 7 shows the use of the improved fluorescent emission materials in an exemplary coding and identification application. A substrate 10 (e.g., paper, plastic, textile, etc.) includes a plurality of regions 12, 14, 16 (e.g., 3 regions) containing different particles in accordance with the foregoing teachings. In general, the particles have radii greater than those associated with conventional quantum dots (e.g., greater than about 15–16 nm). The particles within each region emit a characteristic emission wavelength when excited by a source 18, such as a UV source. The characteristic emissions are detected by a wavelength selective detector 20, which provides electrical signals to a data processor 22. Based on the presence or absence of certain emissions, and/or on a specific set of emissions, the data processor is enabled to verify that the substrate is genuine and/or to uniquely identify the substrate and/or to extract some other pertinent information from the emission wavelengths, such as by using a table lookup procedure. In accordance with these teachings, the particles within a region could be comprised of $CdS_xS_{1-x}$, and in different regions the value of x is made different to thus vary the alloy and to obtain a different emission wavelength, as shown in FIG. 6.

Also as was stated, one or more sets of the particles may contain a dopant that varies the emission wavelength, and further tuning may be accomplished by varying the value of x.

Due to the relatively larger size of the particles, as compared to quantum dots, the disadvantages of quantum dots are alleviated, and the benefits of the use of larger particles (e.g., increase quantum efficiency, etc.) are realized.

Although described above in the context of specific compositions, dimensions and the like, those skilled in the art should appreciate that these are exemplary and indicative of presently preferred embodiments of these teachings, and are not intended to be read or construed in a limiting sense upon these teachings.

Thus, while the invention has been particularly shown and described with respect to preferred embodiments thereof, it will be understood by those skilled in the art that changes in form and details may be made therein without departing from the scope and spirit of the invention.

What is claimed is:

1. A method for obtaining information about an object, comprising steps of:

placing a plurality of regions onto the object, each region emitting a predetermined wavelength of light;

detecting the light; and decoding information from the detected light, wherein
        at least one region is comprised of semiconductor particles having a radius larger than a quantum dot radius for a corresponding semiconductor material, and a chemical composition selected to provide the predetermined wavelength of light, where the semiconductor material is comprised of one of a Group II–VI alloy, or a Group III–V alloy, or a compound comprised of an indirect bandgap material, and wherein the concentrations of the alloy or compound constituent elements are preselected to provide the predetermined emission wavelength.

2. A method as in claim 1, wherein the semiconductor material is further comprised of a dopant.

3. A method as in claim 1, wherein the semiconductor material alloy has the form $AB_xC_{1-x}$, where A, B and C are each a different element.

4. A method as in claim 1, wherein the semiconductor material alloy has the form $AB_xC_{1-x}$, where A, B and C are each a different element, and where in at least two of said plurality of regions the value of x is different.

5. A system for obtaining information about an object, comprising:

a plurality of regions associated with the object, each region emitting a predetermined wavelength of light;

a detector for detecting the light; and a decoder for decoding information from the detected light, wherein
        at least one region is comprised of semiconductor particles having a radius larger than a quantum dot radius for a corresponding semiconductor material, and a chemical composition selected to provide the predetermined wavelength of light, wherein the semiconductor material is comprised of one of a Group II–VI alloy, or a Group III–V alloy, or a compound comprised of an indirect bandgap material, and wherein the concentrations of the alloy or compound constituent elements are preselected to provide the predetermined emission wavelength.

6. A system as in claim 5, wherein the semiconductor material is further comprised of a dopant.

7. A system as in claim 5, wherein the semiconductor material alloy has the form $AB_xC_{1-x}$, where A, B and C are each a different element.

8. A system as in claim 5, wherein the semiconductor material alloy has the form $AB_xC_{1-x}$, where A, B and C are each a different element, and where in at least two of said plurality of regions the value of x is different.

9. A system for obtaining information about a substrate comprising:

a substrate having a plurality of discrete regions thereon, at least one of the discrete regions containing particles, each of the particles having a surface dimension greater than a quantum dot dimension for a corresponding semiconductor material, wherein the particles are pre-selected to emit an associated predetermined emission wavelength;

an excitation source, adapted to provide radiation that causes the particles of a particular region to emit the associated predetermined emission wavelength of the particular region;

a detection unit adapted to detect the associated predetermined emission wavelength from the particles of each region and the detection unit adapted to generate electrical signals as a function of the detected associated predetermined emission wavelength; and a processing unit adapted to receive the electrical signals from the detection unit and process the electrical signals to establish a characteristic of the substrate.

10. A system as in claim 9, farther comprising:

a memory unit, coupled to the processing unit, the memory unit adapted to store data relating to selected characteristics of a plurality of substrates.

11. A system as in claim 9, wherein the particles include $CdS_xSe_{1-x}$.

12. A system as in claim 9, wherein the particles include $ZnS_xSe_{1-x}$.

13. A system as in claim 9, wherein each particle has a surface dimension that exceeds approximately 15 nanometers.

14. A system as in claim 9, wherein at least one region has particles comprised of an indirect bandgap material.

15. A system as in claim 14, wherein the indirect bandgap material is Si.

16. A system as in claim 14, wherein the indirect bandgap material is Ge.

17. A method as in claim 1, wherein the indirect bandgap material is Si.

18. A method as in claim 1, wherein the indirect bandgap material is Ge.

* * * * *